(12) United States Patent
Tsao

(10) Patent No.: US 10,898,385 B2
(45) Date of Patent: Jan. 26, 2021

(54) WOUND DRESSING

(71) Applicant: CORELEADER BIOTECH CO., LTD., New Taipei (TW)

(72) Inventor: Teeming Tsao, New Taipei (TW)

(73) Assignee: CORELEADER BIOTECH CO., LTD., New Taipei (TW)

( * ) Notice: Subject to any disclaimer, the term of this patent is extended or adjusted under 35 U.S.C. 154(b) by 462 days.

(21) Appl. No.: 15/681,635

(22) Filed: Aug. 21, 2017

(65) Prior Publication Data

US 2019/0053951 A1 Feb. 21, 2019

(51) Int. Cl.
*A61F 13/00* (2006.01)

(52) U.S. Cl.
CPC .. *A61F 13/00017* (2013.01); *A61F 13/00029* (2013.01); *A61F 13/00038* (2013.01)

(58) Field of Classification Search
CPC .......... A61F 13/00012; A61F 13/00017; A61F 13/00029; A61F 13/00038; A61F 2013/00238; A61F 2013/00544; A61F 2013/00604; B32B 27/00
USPC ........ 602/42, 43, 44, 45, 48, 55, 76; 28/102, 28/157, 247; 428/37, 108, 113, 152, 911; 112/402; 89/36
See application file for complete search history.

(56) References Cited

U.S. PATENT DOCUMENTS

| | | | | |
|---|---|---|---|---|
| 4,556,440 A | * | 12/1985 | Krueger | B29C 70/16 156/181 |
| 5,807,295 A | * | 9/1998 | Hutcheon | A61F 5/01 602/42 |
| 6,306,483 B1 | * | 10/2001 | Bessey | B29C 51/004 428/175 |
| 2006/0029639 A1 | * | 2/2006 | Morinaga | A61L 27/24 424/424 |
| 2009/0287130 A1 | * | 11/2009 | Lee | A61F 13/36 602/44 |
| 2010/0036334 A1 | * | 2/2010 | Heagle | A61M 1/0088 604/319 |
| 2016/0317353 A1 | * | 11/2016 | Wang | A61F 13/00017 |
| 2017/0208958 A1 | * | 7/2017 | Alletto, Jr. | A47C 27/22 |

* cited by examiner

*Primary Examiner* — Rachael E Bredefeld
*Assistant Examiner* — William T Kao
(74) *Attorney, Agent, or Firm* — Sinorica, LLC

(57) ABSTRACT

Provided is a multi-layered non-woven wound dressing produced by a method including steps of: preparing multiple natural polymeric layers; stacking the multiple natural polymeric layers to form a polymeric structure; preparing multiple natural polymeric threads; and stitching the polymeric structure with the natural polymeric threads to enforce a formed multi-layered non-woven wound dressing and continuous crossing lines to enforce the formed multi-layered non-woven wound dressing to reinforce its longitudinal and transversal tensile strength for a pre-set period of degradation in wound.

12 Claims, 3 Drawing Sheets

WOUND DRESSING

BACKGROUND OF THE INVENTION

1. Field of the Invention

The present invention relates to a non-woven wound dressing, especially to a multi-layered non-woven wound dressing produced by stitching multiple natural polymeric layers.

2. Description of the Prior Art

The tensile strength of the conventional non-woven wound dressing is usually weak. The structure of the conventional non-woven wound dressing comprises a single layer or multiple layers of materials. To enhance the tensile strength of a conventional non-woven wound dressing applied to cavity wound or sinus wound, the conventional non-woven wound dressing is usually made by adding longitudinal lines of stitches formed from a thread and optionally lines of stitches formed from a thread. The materials of the thread used for manufacturing the conventional non-woven wound dressing are usually cellulose, nylon, polyester, elastane or polyurethane. The thread can be impregnated with or without an active agent, such as anti-microbial agent. The conventional non-woven wound dressings are only reinforced by longitudinal stitches and thus vulnerable to the tensile force in the transverse direction. Therefore, they usually break up in the wounds and make dressing removal more time and labor consuming. In addition, because the stitches aim to enhance the strength of dressings, the threads are usually made of non-resolvable materials. Some of them are even inorganic (ex. PE, PU). If they are not cleaned thoroughly and remain in the wound, they may induce rejection reactions of the human body.

SUMMARY OF THE INVENTION

The main objective of the invention is to provide a multi-layered non-woven wound dressing stitched up by natural polymeric yarns, which enhances the resistance of wound dressing to the tensile force in both longitudinal and transversal direction. As a result, the wound dressing can remain as a whole piece without causing the rejection reactions in the human body even if they are accidentally left over in the wound due to breakage.

To achieve the above objective, a multi-layered non-woven wound dressing produced by the steps of:
preparing multiple natural polymeric layers;
stacking the multiple natural polymeric layers to form a polymeric structure;
preparing multiple natural polymeric threads; and
stitching the polymeric structure with the multiple natural polymeric threads to form the multi-layered non-woven wound dressing, and continuous crossing lines penetrating through each layer of multi-layered non-woven wound dressing.

Preferably, the method for producing the multi-layered wound dressing in accordance with the present invention further comprises a step of:
binding each of the multiple natural polymeric layers together after the step of stacking the multiple natural polymeric layers.

Preferably, the mean for binding each of the multiple natural polymeric layers includes, but are not limited to, needle punching, thermal bonding, ultrasonic welding, stitching or glue adhesion.

Preferably, the continuous crossing lines are curved in wave patterns. Each of the wave patterns has alternate crests and troughs, and any two of the adjacent wave patterns are crossed to form a chain of the continuous crossing lines.

Preferably, any two of the adjacent wave patterns intersect at wave nodes, and each of the wave nodes of one of the wave patterns is crossed with each of the wave nodes of another one of the wave patterns.

Preferably, a distance between the crest and the trough of each of the wave patterns is from 0.5 cm to 5.0 cm. A distance between the two nearest wave nodes of each of the wave patterns is from 0.5 cm to 4.0 cm. A distance between the crest of one continuous crossing line and the trough of another continuous crossing line adjacent to said continuous crossing line is from 0 cm to 4.0 cm.

More preferably, the distance between the crest and the trough of each of the wave patterns is 1.5 to 4.0 cm.

Preferably, the continuous crossing lines of the multi-layered non-woven wound dressing are formed by first oblique lines and second oblique lines; the first oblique lines are parallel to each other, the second oblique lines are parallel to each other, and the first oblique lines cross the second oblique lines at crossing points.

More preferably, a first oblique angle of each of the first oblique lines is 30 degrees to 60 degrees against the longitude of the non-woven multi-layer wound dressing, and a second oblique angle of each of the second oblique lines is −30 degrees to −60 degrees against the longitude of the non-woven multi-layer wound dressing.

More preferably, a distance between the adjacent two first oblique lines or the adjacent two second oblique lines is from 0.5 cm to 3.0 cm; numbers of the crossing points in an area of 2 $cm^2$ to 3 $cm^2$ of the multi-layered non-woven wound dressing are from 2 to 4.

More preferably, a distance between the adjacent two first oblique lines or the adjacent two second oblique lines is from 1.0 to 2.0 cm.

More preferably, the first oblique angle and the second oblique angle are 45 degrees and −45 degrees, respectively.

Preferably, the materials of the non-woven multiple natural polymeric layers comprise alginate, chitosan, gelatin, hyaluronic acid, collagen or any combination thereof.

Preferably, the materials of the non-woven multiple natural polymeric threads comprise alginate, rayon, chitosan, gelatin, hyaluronic acid, collagen, bio-compatible natural polymeric fiber or any combination thereof.

Preferably, the average weight per unit area of the multi-layered non-woven wound dressing is from 100 $g/m^2$ to 500 $g/m^2$.

Preferably, each of the polysaccharide natural polymeric threads is made from 100 to 300 fibers. The diameter of the fibers is between 10 to 15 μm.

The tensile strength of the multi-layered non-woven wound dressing produced by the method in accordance with the present invention having continuous crossing lines with the wave patterns or the oblique lines is enhanced both longitudinally and transversely. The multi-layer non-woven wound dressing produced by the method can either be removed as a whole piece from the wound after staying on the wound for a desirable period of time. The thread will not cause immune rejection reaction due to their natural properties. Therefore, the problems of weak tensile strength and the problems of threads left-over in the wound from the conventional non-woven wound dressing can be solved.

DETAILED DESCRIPTION OF THE PREFERRED EMBODIMENTS

Figure 1:
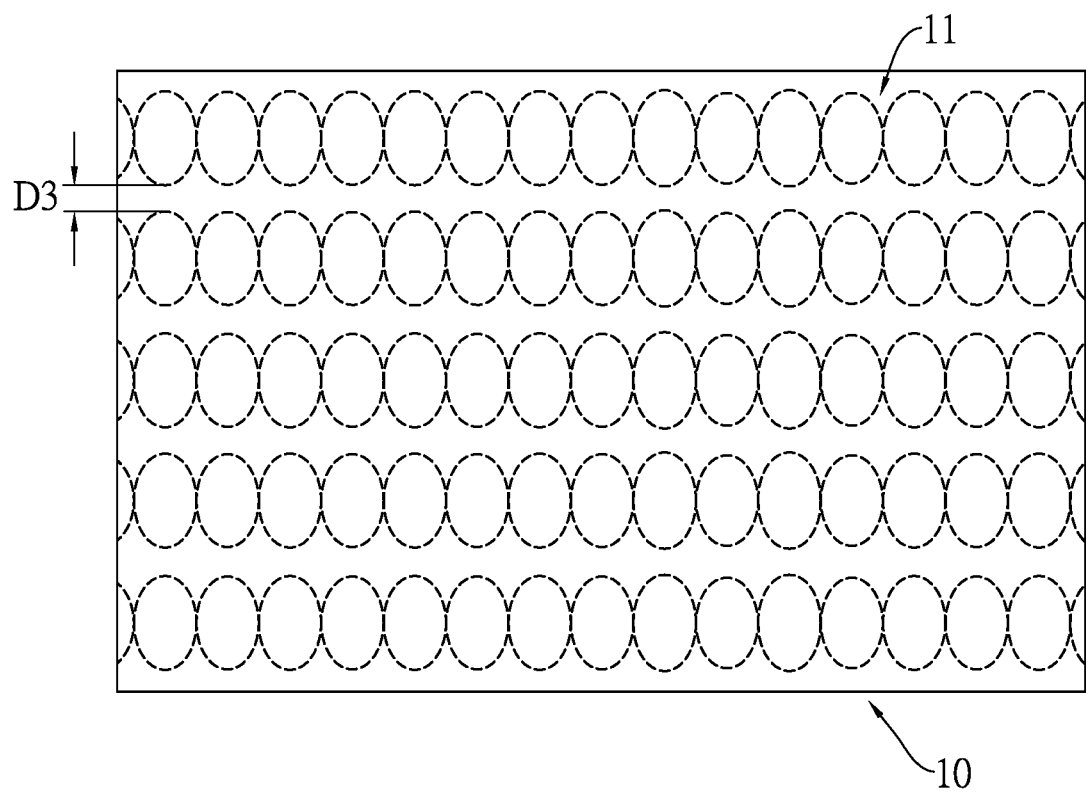
FIG. 1 is a top front view of a first embodiment of a multi-layered wound dressing produced by a method in accordance with the present invention.

With references to FIG. 1, a multi-layered non-woven wound dressing 10 in accordance with a first embodiment of the present invention is produced by a method comprising steps of:

preparing alginate layers made of alginate fibers;
stacking the alginate layers to form an alginate structure;
preparing multiple natural polymeric threads by twisting alginate fiber, collagen fiber or alginate-collagen fiber into the multiple natural polymeric threads; the multiple natural polymeric threads are made from 100 to 3000 fibers, and each of the fiber has a diameter of 10 to 15 μm;
stitching the alginate structure with the alginate or collagen threads to form the multi-layered non-woven wound dressing 10 with continuous crossing lines 11 seen on its surface.

Figure 2:
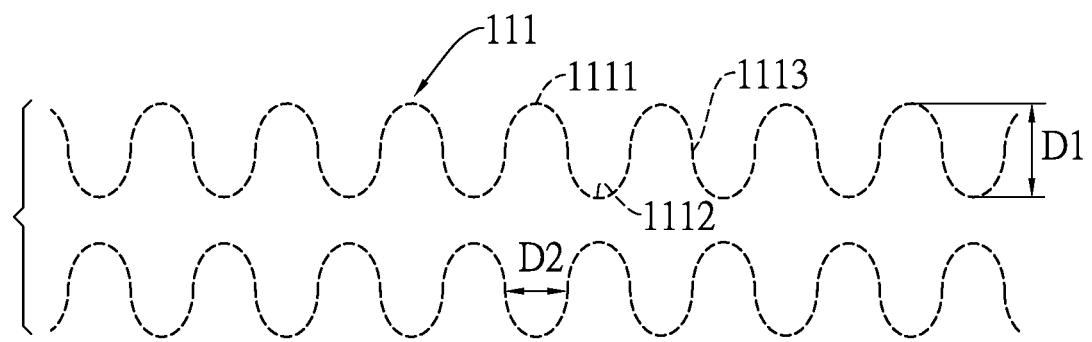
FIG. 2 is an exploded top view of the multi-layered non-woven wound dressing produced by the method in FIG. 1.

With reference to FIGS. 1 and 2, the pattern of the continuous crossing lines 11 of the multi-layered non-woven wound dressing 10 is formed by wave patterns 111. Each of the wave patterns 111 has an alternating pattern of crests 1111 and troughs 1112 as well as wave nodes 1113. Each of the wave nodes 1113 of one of the wave patterns 111 is crossed with each of the wave nodes 1113 of the adjacent wave pattern 111, and two of the adjacent wave patterns 111 are crossed to form a chain of the continuous crossing lines 11. A distance D1 between the crest 1111 and the trough 1112 of each of the wave patterns 111 is 3 cm. A distance D2 between the two nearest wave nodes 1113 of each of the wave patterns 111 is 2.0 cm. A distance D3 between the crest 1111 of the chain of one continuous crossing line 11 and the trough 1112 of another continuous crossing line 11 adjacent to the one continuous crossing line 11 is 1.5 cm. The average weight per unit area of the multi-layered non-woven wound dressing 10 is 200 g/m$^2$.

When using the multi-layer non-woven wound dressing 10, a user cuts the multi-layer non-woven wound dressing 10 into pieces of an appropriate size and covers the wound bed with it.

The multi-layered non-woven wound dressing 10 may enhance the granulation of fibroblast cells and facilitate the secretion of collagen. The collagen released from the collagen threads or alginate-collagen combination threads on the multi-layer non-woven wound dressing 10 to the wound can inhibit the reaction of metalloproteinase and accelerate wound healing.

Figure 3:
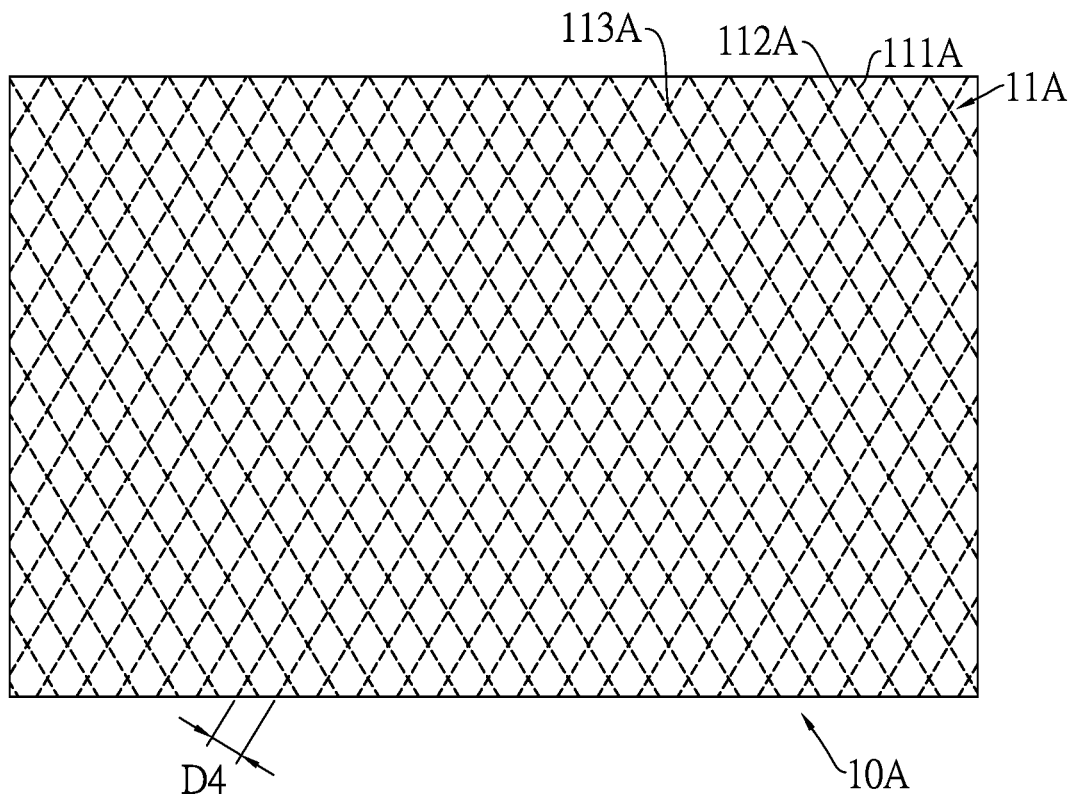
FIG. 3 is a top front view of a second embodiment of the multi-layered non-woven wound dressing produced by the method in accordance with the present invention.

With references to FIG. 3, a multi-layered non-woven wound dressing 10A in accordance with a second embodiment of the present invention produced by the method is similar to the multi-layered non-woven wound dressing 10 produced by the method of the first embodiment. The differences between the first embodiment and the second embodiment include:

The continuous crossing lines 11A of the multi-layered non-woven wound dressing 10A are formed by first oblique lines 111A and second oblique lines 112A. The first oblique lines 111A are parallel to each other, the second oblique lines 112A are parallel to each other, and the first oblique lines 111A cross the second oblique lines 112A at crossing points 113A. A first oblique angle of each of the first oblique lines 111A is 30 degrees to 60 degrees against the longitude of the multi-layer non-woven wound dressing 10A, and a second oblique angle of each of the second oblique lines 112A is −30 degrees to −60 degrees against the longitude of the multi-layer wound dressing 10A. In a preferred embodiment, the first oblique angle and the second oblique angle are 45 degrees and −45 degrees, respectively. A distance D4 between the adjacent two first oblique lines 111A or the adjacent two second oblique lines 112A is from 1.0 to 3.0 cm; preferably, 1.5 cm. The number of the crossing points 113A in an area of 2 cm$^2$ to 3 cm$^2$ of the multi-layered non-woven wound dressing 10A is from 2 to 4.

Even though the numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A multi-layered non-woven wound dressing produced by the steps of:
   preparing multiple natural polymeric layers;
   stacking the multiple natural polymeric layers to form a polymeric structure;
   preparing multiple natural polymeric threads, wherein each of the multiple natural polymeric threads is formed by twisting 300 to 3000 fibers; and
   stitching the polymeric structure with the multiple natural polymeric threads to form the multi-layered non-woven wound dressing, and continuous crossing lines penetrating through each layer of the multi-layered non-woven wound dressing, wherein materials of the multiple natural polymeric threads consist of alginate.

2. The multi-layered non-woven wound dressing as claimed in claim 1, wherein the multi-layered non-woven wound dressing is produced by the method that further comprises a step of:
   binding each of the multiple natural polymeric layers together after the step of stacking the multiple natural polymeric layers.

3. The multi-layered non-woven wound dressing as claimed in claim 2, wherein the means for binding each of the multiple natural polymeric layers comprises needle punching, thermal bonding, ultrasonic welding, stitching or glue adhesion.

4. The multi-layered non-woven wound dressing as claimed in claim 1, wherein the continuous crossing lines are curved in wave patterns; each of the wave patterns has alternate crests and troughs, and any two of the wave patterns, which are adjacent, are crossed to form a chain of the continuous crossing lines.

5. The multi-layered non-woven wound dressing as claimed in claim 4, wherein any two of the adjacent wave patterns intersect at wave nodes, each of the wave nodes of one of the wave patterns is crossed with each of the wave nodes of another one of the wave patterns.

6. The multi-layered non-woven wound dressing as claimed in claim 4, wherein a distance between the crest and the trough of each of the wave patterns is from 0.5 cm to 5.0 cm; a distance between the two wave nodes nearest each other of each of the wave patterns is from 0.5 cm to 4.0 cm; and a distance between the crest of one continuous crossing line and the trough of another continuous crossing line adjacent to said continuous crossing line is from 0 cm to 4.0 cm.

7. The multi-layered non-woven wound dressing as claimed in claim 6, wherein the distance between the crest and the trough of each of the wave patterns is 1.5 cm to 4.0 cm.

8. The multi-layered non-woven wound dressing as claimed in claim 1, wherein the continuous crossing lines of the multi-layered non-woven wound dressing are formed by first oblique lines and second oblique lines; the first oblique lines are parallel to each other, the second oblique lines are parallel to each other, and the first oblique lines cross the second oblique lines at crossing points.

9. The multi-layered non-woven wound dressing as claimed in claim 8, wherein a first oblique angle of each of the first oblique lines is 30 degrees to 60 degrees against the longitude of the multi-layer non-woven wound dressing, and a second oblique angle of each of the second oblique lines is −30 degrees to −60 degrees against the longitude of the multi-layer non-woven wound dressing; a distance between the first oblique lines which are adjacent or the second oblique lines which are adjacent is from 0.5 cm to 3.0 cm; numbers of the crossing points in an area of 2 $cm^2$ to 3 $cm^2$ of the multi-layered non-woven wound dressing are from 2 to 4.

10. The multi-layered non-woven wound dressing as claimed in claim 9, wherein the first oblique angle and the second oblique angle are 45 degrees and −45 degrees, respectively.

11. The multi-layered non-woven wound dressing as claimed in claim 1, wherein the materials of the multiple natural polymeric layers comprise alginate, chitosan, gelatin, hyaluronic acid, collagen or any combinations thereof.

12. The multi-layered non-woven wound dressing as claimed in claim 1, wherein an average weight per unit area of the multi-layered non-woven wound dressing is from 100 $g/m^2$ to 500 $g/m^2$.

* * * * *